(12) United States Patent
Oster

(10) Patent No.: US 8,404,886 B2
(45) Date of Patent: Mar. 26, 2013

(54) PURIFICATION OF 5-SULFOISOPHTHALIC ACID BY THE USE OF AN ACETIC ACID WASH ON A CRUDE CAKE

(75) Inventor: Timothy A. Oster, Batesville, AR (US)

(73) Assignee: Future Fuel Chemical Company, Clayton, MO (US)

( * ) Notice: Subject to any disclaimer, the term of this patent is extended or adjusted under 35 U.S.C. 154(b) by 392 days.

(21) Appl. No.: 12/714,996

(22) Filed: Mar. 1, 2010

(65) Prior Publication Data

US 2010/0298597 A1  Nov. 25, 2010

Related U.S. Application Data

(60) Provisional application No. 61/156,211, filed on Feb. 27, 2009.

(51) Int. Cl.
*C07C 321/00* (2006.01)
*C07C 63/00* (2006.01)

(52) U.S. Cl. ........................ 562/432; 562/485

(58) Field of Classification Search .................. None
See application file for complete search history.

(56) References Cited

U.S. PATENT DOCUMENTS

| | | | |
|---|---|---|---|
| 4,303,577 A | 12/1981 | Ridgway et al. | |
| 6,133,382 A | 10/2000 | Studholme | |
| 6,334,877 B1 | 1/2002 | Studholme | |
| 6,355,835 B1 | 3/2002 | Kulsrestha et al. | |
| 2002/0169273 A1 | 11/2002 | Duan | |
| 2004/0006194 A1 | 1/2004 | Duan | |
| 2004/0242838 A1 | 12/2004 | Duan | |
| 2006/0264665 A1* | 11/2006 | Gibson et al. | 562/485 |
| 2007/0088133 A1 | 4/2007 | Heater | |
| 2007/0208200 A1* | 9/2007 | Parker et al. | 562/485 |
| 2010/0275568 A1 | 11/2010 | Chikatsune et al. | |

FOREIGN PATENT DOCUMENTS

| | | |
|---|---|---|
| CN | 1203909 | 1/1999 |
| CN | 1673450 | 9/2005 |
| CN | 200610043229 | 8/2006 |
| CN | 101279940 | 10/2008 |
| CS | 119642 | 8/1966 |
| CS | 157260 | 12/1973 |
| CS | 157260 | 4/1975 |
| DE | 19382271 | 2/1971 |
| IN | 172789 | 11/1993 |
| IN | WO2009072144 | 6/2009 |
| JP | 48080539 | 10/1973 |
| JP | 51004142 | 1/1976 |
| JP | 1992-247064 | 9/1992 |
| JP | 2004331527 | 11/2004 |
| JP | 2005145836 | 6/2005 |
| WO | WO2011049940 | 4/2011 |

OTHER PUBLICATIONS

Database Caplus Chemical Abstracts Service, Columbus, Ohio, US; Database Accession No. 1980:585973, Abstract of Harada et al., JP 550334421, 1980.*
US Statutory Invention Registration H1760 (Elango, Waradaraj et al.) Nov. 3, 1998.
http://www.xuyechem.com/pages/lisipa.htm (Jun. 15, 2008).
Yu, et al., Synthesis of sodium bis(2-hydroxyethyl) 5-sulfoisophthalate, Huaxue Shijie, 2005, pp. 26-29, vol. 46 Issue 1, China.
Zhao, et al, Synthesis of medium-temperature SIPE, Hecheng Xianwei Gongye, 2001, p. 5-9, vol. 24, Issue 6, China.
Tang, et al., Improvement of the synthetic process of dimethyl 5-sulfoisophthalate sodium salt, Qingdao Keji Daxue Xuebao, Ziran Kexueban 2003, pp. 113-116, vol. 24 Issue 2, China.
Zhang, et al., New Process for the manufacture of dimethyl 5-sulfoisophthalate sodium salt, Jingxi Huagong, 200, pp. 633-636, vol. 17 Issue 11, China.

(Continued)

*Primary Examiner* — Karl J Puttlitz
(74) *Attorney, Agent, or Firm* — Kutak Rock; Stan Baker

(57) ABSTRACT

A method for the purification of 5-sulfoisophthalic acid wherein via the application of an acetic acid wash while said crude cake of 5-sulfoisophthalic acid is filtered.

16 Claims, 2 Drawing Sheets

OTHER PUBLICATIONS

Zhang, Production technique for dimethyl sodiosulfoisophthalate, Juzhi Gongyye Bianjibu, 2002, pp. 20-22, vol. 15, Issue 1, China.

Wu, et al., Study on the production of dyeing modifer SIPM for polyester fiber, Hecheng Xianwei Gongye, 1995, pp. 11-13, vol. 18, Issue 2, China.

Wu, et al., Synthesis of dyeing improver for cationic dye dyeable polyester fibers, Dalian Ligong Daxue Xuebao, 1995, pp. 434-436, vol. 35 Issue 3, China.

Jiang, et al., Synthesis of sodium 3,5-dimethoxycarbonyl benzene sulfonate, Huagong Shikan, 2000, pp. 21-23, vol. 14, Issue 5, China.

Zhang, et al., Synthesis of sodium 5-sulfodimethylisophthalate, Jingxi Huagong Bianjibu, 1998, pp. 29-41, vol. 15, Issue 3, China.

Li, et al., Synthesis of sodium dimethyl 5-sulfoisophthalate, Jingxi Huangong Bianjibu, 2003, pp. 50-52, vol. 20, Issue 1, China.

* cited by examiner

PURIFICATION OF 5-SULFOISOPHTHALIC ACID BY THE USE OF AN ACETIC ACID WASH ON A CRUDE CAKE

CROSS REFERENCE TO RELATED APPLICATION(S)

This application claims benefit of U.S. Provisional Patent Application Ser. No. 61/156,211 filed Feb. 27, 2009, the entire disclosure of which is herein incorporated by reference.

BACKGROUND

1. Field of the Invention

This disclosure relates to the field of chemical purification. In particular, to the field of purifying 5-sulfoisophthalic acid by use of an acetic acid wash.

2. Description of the Related Art 5-sulfoisophthalic acid is a molecule which can be used in treating nylon-based textiles with the purpose of achieving stain resistance due to the ability of the 5-sulfoisophthalic acid to act as a topical "stain blocker" by associating with, and thereby blocking access to, acid dye sites or for other uses known to those of ordinary skill in the art. In order to obtain 5-sulfoisophthalic acid, traditionally the sulfonation of isophthalic acid using 30% oleum is performed. This produces a mixture which includes impurities. To remove the impurities solvents have been used to wash the 5-sulfoisophthalic acid.

There are a number of common problems inherent to the solvents which have been used in this process which include the following. First, solvents such as water and acetone are known to dissolve a significant quantity of the product as they are removing impurities. This decreases the resultant yield of product from each production run or batch. Other solvents, such as methanol, react with the product to produce undesired esters. Still further solvents, such as toluene and heptane, do not displace the primary impurities of the solution. Thus, the generally used solvents and purification processes currently employed in the art are either ineffective or require large quantities of the solvent to remove the impurities, additional equipment, excess labor, and increased cycle time; all while resulting in a lowered yield of the final product.

Czech Patent CS 157260 19750415, indicates in its abstract that sulfonated aromatic carboxylic acids (including 5-HSIPA) can be purified by being digested with an acetic acid which removes sulfonic acids, carboxylic acids and residual acid. Digesting (re-slurrying or re-pulping) generally involves the complete isolation of the crude product, re-introduction into a digesting unit with enough solvent to allow adequate agitation, a hold time, and a re-isolation of the product. While this disclosure is a step forward from the conventional solvents and purification processes previously discussed because it can produce increased yield, there are still numerous problems. For example, the crude product still needs to be isolated in this process, a large quantity of acetic acid is still needed to displace the impurities, and additional labor, equipment, and time are required, resulting in increased production costs.

SUMMARY

The following is a summary of the invention in order to provide a basic understanding of some aspects of the invention. This summary is not intended to identify key or critical elements of the invention or to delineate the scope of the invention. The sole purpose of this section is to present some concepts of the invention in a simplified form as a prelude to the more detailed description that is presented later.

Because of these and other problems in the art, described herein are, among other things, methods of purification that involve the use of glacial acetic acid to wash a crude cake of 5-sulfoisophthalic acid for the removal of impurities such as sulfuric acid, water, etc. In certain embodiments, the crude product cake can be isolated utilizing a centrifuge, a filter box, or any other solids isolation equipment that allows for a solvent wash.

In one embodiment of the disclosed methods for purification by the use of an acetic acid wash on a crude cake, the method comprises the steps of: (1) filtering a crude product cake via solids isolation equipment; (2) washing the crude product cake with acetic acid in the solids isolation equipment; and (3) drying the crude product cake.

In one embodiment of this method, the crude cake is 5-sulfoisphthalic acid.

In yet another embodiment of this method, the solids isolation equipment is a centrifuge.

In another embodiment of the disclosed methods for the purification of 5-sulfoisphthalic acid by the use of an acetic acid wash on a crude cake, the method comprises the steps of: (1) cooling a crude 5-sulfoisphthalic acid cake comprising 5-sulfoisphthalic acid, sulfuric acid, and water to about 165° C.; (2) quenching the crude 5-sulfoisphthalic acid cake into about 5° C. water to create an aqueous 5-sulfoisphthalic acid solution while keeping the aqueous 5-sulfoisphthalic acid solution below about 120° C.; (3) taking the 5-sulfoisphthalic acid solution to reflux; (4) distilling water from the 5-sulfoisphthalic acid solution; (5) cooling the 5-sulfoisphthalic acid solution; (6) isolating the 5-sulfoisphthalic acid solution by filtration and pulling; (7) washing the crude 5-sulfoisphthalic acid cake comprising 5-sulfoisphthalic acid, sulfuric acid, and water via solids isolation equipment with acetic acid to remove the sulfuric acid and the water without removal of the 5-sulfoisphthalic acid cake from the solids isolation equipment; pulling the acetic acid wash; and drying a purified crude 5-sulfoisphthalic acid wet solid.

In yet another embodiment of the disclosed methods for the purification of 5-sulfoisphthalic acid by the use of an acetic acid wash on a crude cake, the method comprises the steps of: (1) sulfonating isophthalic acid oleum; (2) isolating a resultant crude 5-sulfoisphthalic acid; (3) cooling the crude 5-sulfoisphthalic acid; (4) quenching the crude 5-sulfoisphthalic acid to create an 5-sulfoisphthalic acid/water mixture; (5) heating the 5-sulfoisphthalic acid/water mixture to reflux; (6) distilling water from the 5-sulfoisphthalic acid/water mixture; (7) holding the 5-sulfoisphthalic acid/water mixture at a reflux temperature; (8) removing a mantle from the aqueous 5-sulfoisphthalic acid/water mixture; (9) cooling the 5-sulfoisphthalic acid/water mixture; (10) holding the 5-sulfoisphthalic acid/water mixture at a cooled temperature; (11) cooling the 5-sulfoisphthalic acid/water mixture; (12) cooling the 5-sulfoisphthalic acid/water mixture with an ice bath; (13) holding the 5-sulfoisphthalic acid/water mixture at a cooled temperature; (16) filtering the 5-sulfoisphthalic acid/water mixture; (17) pulling the 5-sulfoisphthalic acid/water mixture; (18) washing a filtrate of the 5-sulfoisphthalic acid/water mixture via solids isolation equipment with acetic acid without removal of the filtrate from the solids isolation equipment; (19) pulling the filtrate; and (20) drying the filtrate.

In an embodiment of this method, in the step of heating the 5-sulfoisphthalic acid/water mixture is heated to about 137.1° C.

In another embodiment of this method, in the first step of holding the 5-sulfoisphthalic acid/water mixture is held at 137.1° C. for forty-five minutes.

In yet another embodiment of this method, in the first step of cooling the 5-sulfoisphthalic acid/water mixture is cooled to 55° C. over a forty-five minute time period.

In still another embodiment of this method, in the second step of holding the 5-sulfoisphthalic acid/water mixture is held at 55° C. for one hundred and thirty-five minutes.

In another embodiment of this method, in the second step of cooling the 5-sulfoisphthalic acid/water mixture is cooled to 29.4° C.

In yet another embodiment of this method, in the third step of cooling the 5-sulfoisphthalic acid/water mixture is cooled to 25° C. with an ice bath.

In another embodiment of this method, in the third step of holding the 5-sulfoisphthalic acid/water mixture is held at 25° C. for sixty minutes.

In yet another embodiment, this step of pulling the 5-sulfoisphthalic acid/water mixture is pulled for ten minutes.

In another embodiment, in the said second step of pulling the filtrate is pulled for ten minutes.

In yet another embodiment of this method, in the step of drying the filtrate is dried at 90° C. to 130° C. for twelve hours.

In a final embodiment of this method, the step of sulfonating, the isophthalic acid is sulfonated with 30% oleum at about 190 to 220° C. for six hours.

DESCRIPTION OF THE PREFERRED
EMBODIMENT(S)

The following detailed description illustrates by way of example and not by way of limitation. Described herein, among other things, is a new process for the purification of 5-sulfoisophthalic acid, in one embodiment by use of an acetic acid wash on a crude cake.

Figure 1:
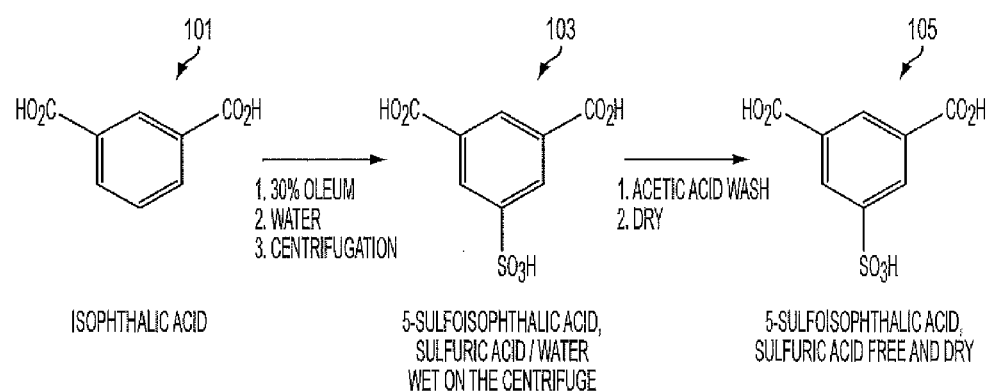
FIG. 1 provides a process flow diagram for an embodiment of the disclosed preparation and purification of 5-sulfoisophthalic acid.

This process, in its simplified form, comprises: the filtering of a crude product cake while supplying an acetic acid wash on said crude product cake. One embodiment of this process for the purification process is shown in the process molecular diagram flow chart of FIG. 1.

As a preliminary matter, an embodiment of a chemical synthesis process to generate 5-sulfoisophthalic acid, 5-HSIPA in its unpurified form will be discussed. However one of ordinary skill would recognize that any methodology may be used. 5-sulfoisophthalic acid, in an embodiment, may be formed from the sulfonation of isophthalic acid (101) using 30% oleum at about 190 to 220° C. for about 6 hours. The resultant matter is then isolated with a filtration or isolation device such as, but not limited to, a centrifuge to remove sulfuric acid and water. At this stage, the second molecule of FIG. 1 has been produced and the 5-sulfoisophthalic acid exists in its unpurified form. While this process is acceptable for the preparation of crude 5-sulfoisophthalic acid, it is used only for exemplary purposes to more fully describe the purification method disclosed herein. Stated differently, the purification process described herein is not only for the purification of 5-sulfoisophthalic acid. Rather, this disclosure contemplates that the disclosed purification method can be used in any chemical process which requires purification for the removal of impurities.

A general description of the purification process described herein is as follows. First, the crude product cake is filtered while supplying an acetic acid wash to provide for purification as opposed to a digestion process, which requires re-slurrying. The acetic acid wash can be performed on the cake without removal of the cake from the isolation equipment and with a relatively simple procedure (which will be described in detail herein). Besides its simplicity, the acetic acid wash on the crude cake is beneficial because the wash process does not make the cake sticky or hard as compared to the digestion and re-slurrying techniques that were previously used in the art. Further, it does not result in the dissolving of a significant quantity of the product as the impurities are removed. Thus, the resultant purified 5-sulfoisophthalic acid is easier to work with, does not have the reduction in yield common in the use of other solvents, and has been purified to provide a more workable form.

While the above provides a general description of the purification process disclosed herein, the description below provides for specific examples of how the process can be performed. However, before the process of this disclosure is more fully described herein, it is important to note that additional steps may be performed in certain embodiments. Further, while certain times, temperatures, and concentrations are disclosed in this description, it is contemplated that these values can be varied as would be understood by those of skill in the art to achieve comparative quality and yield of 5-sulfoisophthalic acid (or any other chemical process which requires purification for the removal of impurities).

In an embodiment of the purification process disclosed herein, a crude reaction mass, like 5-sulfoisophthalic acid with similar impurities such as water and sulfuric acid, is cooled and quenched in water. Next, the aqueous chemical acid solution like 5-sulfoisophthalic acid with similar impurities such as water and sulfuric acid is taken to reflux, and water is distilled from the solution by a distillation method known to those of skill in the art. Then, the mixture is held at a reflux temperature for a certain holding time period. After the holding period has ended, the mantle is removed and the mixture is slowly cooled and held at a temperature for a given period of time. Then the mixture is allowed to slowly cool further, before it is added to an ice bath (or other method known to those of skill in the art to cool a chemical solution) for further cooling. Once the desired temperature is achieved in the ice bath, the solution is held at said temperature for a given period of time. The resultant crude product like 5-sulfoisophthalic acid with similar impurities such as water and sulfuric acid, is then isolated by a filtration method known to those of skill in the art and pulled by a method known to those of skill in the art for a given period of time. Generally, the use of any solids isolation equipment that allows for a solvent wash which is known to those of skill in the art is contemplated in this step.

After filtration and pulling is complete, and preferably without removal of the cake from the filter, the filtrate is washed with acetic acid to remove the impurities present in the crude product. In some embodiments, it is contemplated that the filtrate can be used as a co-product and the acetic acid wash-filtrate can be recovered or incinerated. Then the wash is pulled through by pulling method known to those of skill in the art. The purified crude, acetic acid wet solid is then dried to the appropriate water level using a drying technique known to those of skill in the art. Then, once dried, the product can be unloaded into a desired container as known to those of skill in the art for further sample testing.

In an embodiment where the crude reaction mass is 5-sulfoisophthalic acid, the purification process would generally proceed as follows. First, the 5-sulfoisophthalic acid reaction of FIG. 1 would be cooled to about 165° C. and quenched into about 5° C. water, keeping the unit containing the water below about 120° C. Next, the aqueous 5-sulfoisophthalic acid solution is taken to reflux, slowly cooled to about 55° C., held at about 55° C. for two hours and further cooled to about 25° C. The crude product is then isolated by filtration and washed with about 20° to 25° C. acetic acid to remove the impurities, such as residual sulfuric acid and water. It is contemplated that the filtrate can be used as a co-product and the acetic acid wash-filtrate recovered or incinerated. The crude, acetic acid wet solid is then dried to the appropriate water level. A rough estimate of the appropriate water level is about <1.0%, although isolation of the hydrate may also be possible. Once dried, the product can be unloaded into a designated container, such as a drum, bag, bulk bag, or other storage container known to those of skill in the art.

It is noted that the problems of the prior art (e.g., dissolving of the product, the production of esters, the failure to effectively displace the impurities, the isolation of the crude product, the large quantity of the acetic acid needed to displace the impurities, and the additional labor, equipment and time that are required) are not problems of the disclosed processes of the present application. In the present purification processes the chemical, such as 5-sulfoisophthalic acid, is purified with a high yield and at less manufacturing expense. Specifically, the value of the disclosed purification processes which use acetic acid as a purification solvent during filtration are that: (1) it does not dissolve a significant quantity of the product (as with water and acetone); (2) it does not react with the product to form esters (as with methanol); (3) it effectively displaces the primary impurity sulfuric acid; (4) it does not cause the centrifuge cake to become sticky or hard; (5) unlike the digestion or reslurring processes of the prior art the purification occurs on the centrifuge without the need to isolate the crude product; (6) less acetic acid is needed to displace the impurities; (7) the product yield is higher than all the methods of the prior art.

Example 1

Figure 2:
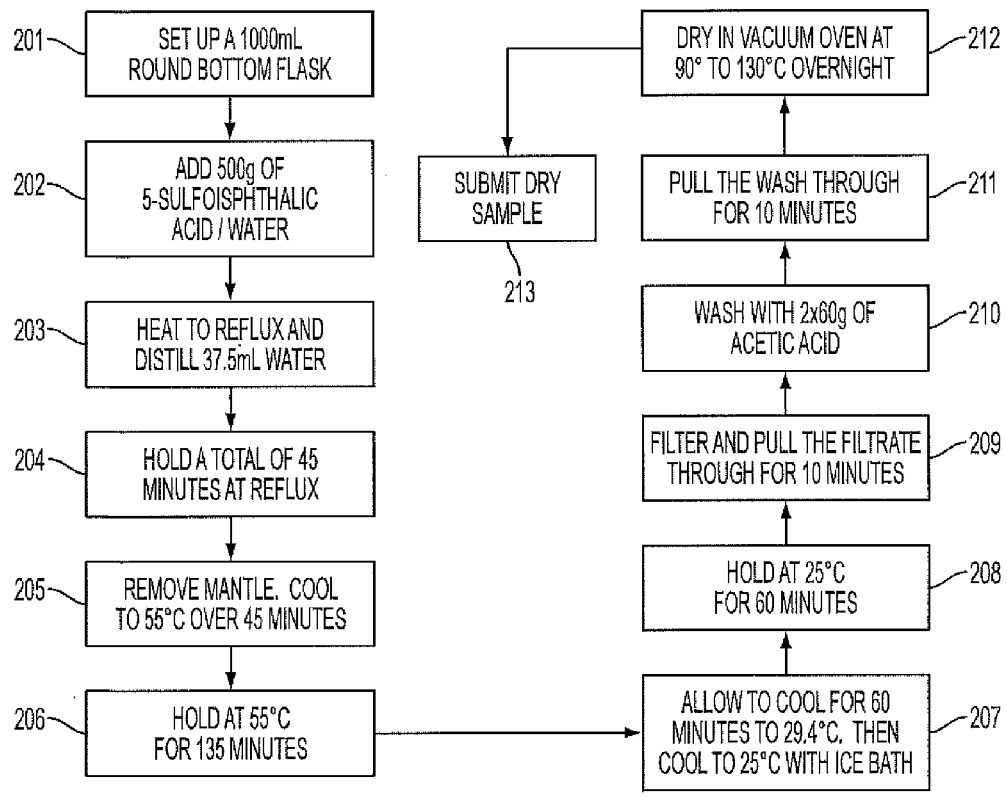
FIG. 2 provides an embodiment of an exemplary step-by-step bench process of the disclosed purification process.

FIG. 2 shows a series of steps for an example of the disclosed purification method as could be performed in a laboratory setting. This process is generally a bench procedure and therefore exemplary of what might be performed in production. It would be understood by one of ordinary skill in the art how this example can be adapted to standard commercial operating processes. Further, for the purpose of this disclosure, it is noted that the distillation and volume conditions discussed in this embodiment are not determinative, and any functional distillation or volume conditions known to those of skill in the art are contemplated in the processes of this disclosure. Moreover, it is inherent that any specifically identified flask or other equipment is not determinative. Any piece of equipment known to those of skill in the art that can properly and effectively function in the given step of the disclosed process is also contemplated. Lastly, it should be noted that while this purification process is described for use on 5-sulfoisophthalic acid, it is contemplated that the purification method can be used in any chemical process which requires purification for the removal of impurities. Thus, the use of 5-sulfoisophthalic acid should be seen as only exemplary, and not in anyway limiting.

To begin, in step (201), a 1000 mL roundbottom flask, or other comparable container known to those of skill in the art, is set up.

Next, in step (202), about 500 grams of 5-sulfoisophthalic acid, approximately 34% in water, is added to the roundbottom flask.

Then, in step (203), the 5-sulfoisophthalic/water mixture is heated to a reflux, and about 37.5 mL of water is distilled by any distillation method known to those of skill in the art.

Following the reflux and distillation, in step (204), the mixture is held a total of about 45 minutes at the reflux temperature, a temperature at or around 137.1° C.

After the holding time period has ended, the mantle is removed in step (205) and the mixture is cooled to about 55° C. over about a 45 minute period.

After the cooling period, in step (206), the mixture is held at about 55° C. for about 135 minutes.

Then, in step (207), the mixture is allowed to cool for about 60 minutes to a temperature at or about 29.4° C.

Once a temperature of 29.4° C. is obtained, the mixture is then cooled to about 25° C. with an ice bath, or by another method of cooling known to those of skill in the art.

Following the ice bath, in step (208), the mixture is held at 25° C. for about 60 minutes.

Next, in step (209), the mixture is filtered on a standard laboratory sintered-glass funnel, or by any other acceptable filtration method known to those of skill in the art.

After filtration, the mixture is pulled for about 10 minutes. The filtrate weight in this step (209) is at or about 132.6 grams.

After the step of filtration and pulling, in step (210), the filtrate is washed with about 2×60 g of glacial acetic acid without removal of the cake from the filter.

Next, in step (211), the wash is pulled through for 10 minutes. It is contemplated that the wash-filtrate weight in this step is at or about 132.6 grams.

After the step of pulling is completed, in step (212), the mixture is dried in a vacuum oven, or other machine known in the art for drying a mixture, at about 90° C. to 130° C. overnight.

In the final step (213), the dry sample is complete and submitted for analysis via an applicable method known to those of ordinary skill in the art. In this example, the dry sample had a product wet weight of about 139.4 grams, a product dry weight of about 128.8 grams, about 92.4% of solids, about 99.88% of total acidity, about 0.47% of water, 0.12% of H2SO4 as sulfate, APHA Color of 14, and a percent yield of about 81.3%.

While the invention has been disclosed in connection with certain preferred embodiments, this should not be taken as a limitation to all of the provided details. Modifications and variations of the described embodiments may be made without departing from the spirit and scope of the invention, and other embodiments should be understood to be encompassed in the present disclosure as would be understood by those of ordinary skill in the art.

The invention claimed is:

1. A method of purifying 5-sulfoisophthalic acid comprising the steps of:
    obtaining a crude cake of 5-sulfoisophthalic acid having a sulfur compound as an impurity, and
    washing said crude cake with acetic acid.

2. The method of claim 1 wherein said crude cake of 5-sulfoisophthalic acid contains sulfuric acid as an impurity.

3. The method of claim 1 wherein the step of obtaining a crude cake of 5-sulfoisophthalic acid comprises filtering a crude product of 5-sulfoisophthalic acid using solids isolation equipment.

4. The method of claim 1 further comprising the prior step of sulfonating isophthalic acid to obtain 5-sulfoisophthalic acid.

5. The method of claim 1 further comprising the step of recovering and recycling said acetic acid.

6. The method of claim 1 wherein the washing step is repeated.

7. The method of claim 3 wherein the washing step occurs while the crude product cake remains in the solids isolation equipment.

8. A method of manufacturing 5-sulfoisophthalic acid comprising the steps of:
   sulfonating isophthalic acid to form 5-sulfoisophthalic acid,
   isolating 5-sulfoisophthalic acid to form a crude cake;
   washing the crude cake with acetic acid; and
   drying the washed crude cake.

9. The method of claim 8 wherein the sulfonating step comprises contacting isophthalic acid with sulfuric acid.

10. The method of claim 8 wherein the isolating step and the washing step occur in the device utilized in the isolating step.

11. The method of claim 8 wherein said acetic acid is recovered and recycled.

12. A method of manufacturing 5-sulfoisophthalic acid comprising the steps of:
    sulfonating isophthalic acid to form a 5-sulfoisophthalic acid product,
    isolating said 5-sulfoisophthalic acid product to form a crude cake of 5-sulfoisophthalic acid product;
    washing the crude cake with a liquid wherein said liquid does not dissolve a significant quantity of the product but is sufficiently polar to remove ionizable impurities from the product; and
    drying the product wherein the wash liquid is acetic acid.

13. The method according to claim 12 wherein the steps of isolating and washing occur in the device utilized in the isolation step.

14. The method according to claim 12 wherein the impurity is a sulfur compound.

15. The method according to claim 12 in which the acetic acid is recovered and recycled.

16. The method according to claim 12 wherein the wash liquid does not significantly ionize the 5-sulfoisophthalic acid product.

\* \* \* \* \*